(12) United States Patent
DiTizio et al.

(10) Patent No.: US 8,361,501 B2
(45) Date of Patent: *Jan. 29, 2013

(54) NON-ADHESIVE ELASTIC GELATIN MATRICES

(75) Inventors: Valerio DiTizio, Toronto (CA); Frank DiCosmo, Richmond Hill (CA); Yuehua Xiao, Toronto (CA)

(73) Assignee: Covalon Technologies, Inc., Mississauga, Ontario ( * ) Notice: Subject to any disclaimer, the term of this patent is extended or adjusted under 35 U.S.C. 154(b) by 702 days.

This patent is subject to a terminal disclaimer.

(21) Appl. No.: 11/152,367

(22) Filed: Jun. 15, 2005

(65) Prior Publication Data

US 2006/0068013 A1 Mar. 30, 2006

Related U.S. Application Data

(60) Provisional application No. 60/614,414, filed on Sep. 30, 2004.

(51) Int. Cl.
*A61K 9/70* (2006.01)

(52) U.S. Cl. ..................................... 424/484

(58) Field of Classification Search .................. None
See application file for complete search history.

(56) References Cited

U.S. PATENT DOCUMENTS

| | | | |
|---|---|---|---|
| 3,491,760 A | 1/1970 | Bernhard | |
| 4,703,108 A | 10/1987 | Silver | |
| 4,970,298 A | 11/1990 | Silver | |
| 5,550,197 A | 8/1996 | Valpey | |
| 5,744,545 A | 4/1998 | Rhee | |
| 6,132,785 A | 10/2000 | Collinge | |
| 6,228,383 B1 | 5/2001 | Hansen | |
| 6,475,516 B2 | 11/2002 | DiCosmo et al. | |
| 6,475,518 B1 | 11/2002 | Baumgart | |
| 2002/0131933 A1* | 9/2002 | Delmotte | 424/1.11 |
| 2003/0039695 A1* | 2/2003 | Geistlich et al. | 424/484 |

FOREIGN PATENT DOCUMENTS

| | | |
|---|---|---|
| CA | 2140053 | 1/1995 |
| EP | 0 680 990 A1 | 11/1995 |
| WO | WO 93/21908 | 11/1993 |
| WO | WO 98/46287 | 10/1998 |
| WO | WO 01/24839 | 4/2001 |

OTHER PUBLICATIONS

Kuijpers et al. "Cross-linking and characterisation of gelatin matrices for biomedical applications", J Biomater Sci Polymer Edn, 11(3), p. 225-243, 2000.*
Leffler, CC and Muller, B.W.; "Chitosan-gelatin sponges for controlled drug delivery: the use of ionic and non-ionic plasticizers", S.T.P. Pharma Sciences, 10(1), p. 105-111, 2000.*
Zeeman et al., Biomaterials, 20, p. 921-931, 1999.*
Defintion of adhesive from dictionary.com, accessed Jun. 15, 2011.*
Defintion of adherent from dictionary.com, accessed Jun. 15, 2011.*
Sigma Product 49781 information, accessed Jan. 25, 2012.*
International Journal of Pharmaceutics, 2000, 194, 229-237; Leffler et al.
Biomaterials, 1999, 20, 409-417; Choi et al.
Choi, Y., et al. "Study on gelatin-containing artificial skin: I. Preparation and characteristics of novel gelatin-alginate sponge", Biomaterials 20 (1999) pp. 409-417.
Leffler, C., et al. "Influence of the acid type on the physical and drug liberation properties of chitosan-gelatin sponges" Int. Journal of Pharmaceutics 194 (2000) pp. 229-237.

* cited by examiner

*Primary Examiner* — Nissa Westerberg
(74) *Attorney, Agent, or Firm* — Knobbe Martens Olson & Bear LLP (57) ABSTRACT

The present invention is a substantially non-adhesive elastic gelatin matrix. The matrix is both non-adhesive to wounds, tissues and organs and is also elastic such that it is flexible. The matrix is a lyophilized mixture of protein(s), polymer(s), cross-linking agent(s) and optional plasticizer(s). The invention also provides methods for making the non-adhesive elastic gelatin matrix.

16 Claims, 3 Drawing Sheets

NON-ADHESIVE ELASTIC GELATIN MATRICES

REFERENCE TO RELATED APPLICATIONS

This application claims the benefit of priority to U.S. Provisional Application No. 60/614,414, filed Sep. 30, 2004.

FIELD OF THE INVENTION

The present invention relates to non-adhesive elastic matrices. More specifically, the present invention relates to non-adhesive cross-linked elastic gelatin matrices, and the method of making the same. The matrices can be provided in a variety of configurations not limited to wound dressings, wound barriers, tissue and vascular coverings. The matrices can also be made to incorporate a variety of pharmaceuticals, chemicals and other agents. Further, the non-adhesive elastic matrices of the present invention can be used alone, or in conjunction with other materials.

BACKGROUND TO THE INVENTION

Gelatin sheets, collagen sheets and sponges are a group of biomaterials that have been used extensively in the medical field. They are dry and absorb and retain large amounts of water. This group of biomaterials is both biocompatible and biodegradable causing little or no inflammation. These biomaterials are useful as wound dressings, artificial skin scaffolds and therapeutic drug delivery devices, whereby the biomaterials can retain therapeutics and deliver such therapeutics to appropriate cells and tissues, as exemplified in Applicant's U.S. Pat. No. 6,475,516.

Gelatin and collagen sheets as provided by the prior art are typically inelastic and may have toxic properties. For example, U.S. Pat. No. 3,491,760 describes a pliable, but inelastic, adhesive multilayer wound covering composed of collagen or gelatin which is "foamed" using air bubbles, treated with a plasticizer (glycerol), cross-linked with a 4% glutaraldehyde solution, and the resulting gel film covered with an adhered cover layer. As is generally known collagen and gelatin matrices cross-linked with glutaraldehyde show residual toxicity.

Gelatin sponge materials such as Gelfoam™, are also known. These materials are absorbable, sterile and water insoluble and used to control bleeding during surgery and may also be provided in a powder format. The material is non-elastic. Another non-elastic gelatin sponge currently used is Surgifoam™. Gelfim™ is a non-elastic material obtained from a formaldehyde cross-linked gelatin solution.

Hydrolyzed collagen, also known as gelatin, has been used as a vehicle for the delivery of therapeutics when covalently attached to the surface of tubular medical devices such as catheters and stents as described in Applicant's U.S. Pat. Nos. 6,132,765 and 6,228,393. The material is hydrated and minimally elastic.

Several patents describe cross-linked inelastic collagen materials such as for example U.S. Pat. Nos. 4,703,108, 4,970,298, 5,550,187, 5,744,545, and 6,132,765.

Sehal and Vijay (Anal. Biochem. 218: 87-91, 1994) describe a method for water-soluble carbodiimide-mediated amidation by using 1-ethyl-3-[3-dimethylaminopropyl carbodiimide (EDC)/N-hydroxy succinimide (NHS). The method is known to cross-link collagen, gelatin and other proteins. However, the resultant matrices are not elastic.

Choi et al. (Biomaterials 20: 409-41, 1999) describe the fabrication of a gelatin-containing artificial skin that contains gelatin and alginate and is cross-linked with EDC. A soluble sponge was immersed in a solution of acetone:water (9:1 by volume) containing 20-100 mg EDC and cross-linked for 24 hr. The EDC when dissolved in water is stated to be deactivated and rapidly loses its cross-linking ability and thus the EDC was dissolved in 90% acetone. The matrix material produced is inherently inelastic.

In the pharmaceutical industry, soft elastic gelatin capsules or "Softgels" are made from a gelatin solution that is plasticized with propylene glycol, sorbitol, glycerin or other approved mixtures. However, the gelatin in the softgel capsules is not cross-linked in order that the capsules remain soluble when ingested. Furthermore, softgel capsules lack elasticity and resistance to the action of degradative processes such as increased temperature and mild enzymatic action.

There is a need to produce gelatin matrices that are elastic, and have appreciable tensile strength while not being prone to becoming hard and brittle.

SUMMARY OF THE INVENTION

The present invention provides substantially non-adhesive, proteinaceous, elastic matrices for a variety of clinical uses. More specifically, the present invention provides substantially non-adhesive, elastic gelatin matrices for use in a variety of applications not limited to, wound barriers, wound dressings, surgical dressings, wraps and in therapeutic drug and/or chemical agent delivery. The present invention also provides a novel method for making the non-adhesive, elastic gelatin matrices of the invention.

In accordance with an aspect of the present invention is a non-adhesive elastic gelatin matrix. The matrix is both non-adhesive and elastic such that it is flexible. The matrix is lyophilized such that it does not contain substantial amounts of solvent and comprises a mixture of collagen or denatured collagen, biocompatible polymers, cross-linking agent(s) and optional plasticizer.

In accordance with another aspect of the present invention is a lyophilized non-adhesive elastic gelatin matrix.

In accordance with another aspect of the present invention is a non-adhesive elastic protein matrix, the matrix comprising;

a mixture of protein comprising collagen and/or gelatin, biocompatible polymers, one or more cross-linking agents. In aspects, the mixture may further comprise one or more plasticizers. In other aspects, the mixture is lyophilized.

In aspects, collagen or denatured collagen, i.e. gelatin is used alone as the protein component of the matrix. In alternative aspects, collagen and gelatin are used in combination as the protein component of the matrix.

In accordance with another aspect of the present invention is a non-adhesive elastic gelatin matrix, the matrix comprising;

a mixture of protein comprising collagen and/or gelatin and biocompatible polymers comprising alginate, polyethylene glycol and poly-L-lysine, wherein said polymers are cross-linked with one or more cross-linking agents and said mixture is lyophilized. In aspects, the mixture may further comprise one or more plasticizers.

In aspects, the collagen can be used alone or denatured collagen, i.e. gelatin used alone or in combination.

In accordance with another aspect of the present invention, there is provided a method for making a non-adhesive elastic gelatin matrix, the method comprising:

lyophilizing a frozen solution comprising at least one protein, at least one biocompatible polymer and at least one cross-linking agent for a time effective to substantially remove the solvent. In aspects, the solution also comprises a plasticizer.

In accordance with still another aspect of the present invention is a method for making a non-adhesive elastic gelatin matrix, the method comprising:
(a) heating a protein solution;
(b) adding one or more biocompatible polymers to (a);
(c) adding at least one cross-linking agent to (b);
(d) cooling (c) and lyophilizing.

In aspects of the invention, the protein of (a) is gelatin and in other aspects is a mixture of gelatin and collagen. A plasticizer may additionally be added to (b) and/or (c). Furthermore, one or more of a pharmaceutical, chemical or other agent may be added before and/or after the cross-linking reaction of step (c). For example, silver ions, metallic silver or a silver salt may be added to the matrix for the treatment of burns or other trauma to minimize and/or inhibit infection. The matrix may be fabricated as a covering such as wound barrier, wound dressing, vascular wrap and combinations thereof. The matrix may also be fabricated as a sponge. The matrix of the invention may be further used to reduce chronic inflammation, absorb exudates and/or promote a moist wound environment. The matrix of the invention may also have incorporated therein a chemical or other agent that is delivered to a desired tissue for at least one of exfoliation and treatment of age related conditions in mammals.

In aspects of the invention, the non-adhesive elastic gelatin matrix may be formed around a web or fibril support. Still in other aspects of the invention, the gelatin matrix of the invention may be used in conjunction with polymer sheets, films, threads or membranes and meshes of silicone, polyurethane, polyethylene, Dacron™, nylon, silk, cellulose and mixtures thereof.

In other aspects of the present invention, the non-adhesive elastic gelatin matrix may be provided as an occlusive device comprising an occlusive structure and the substantially non-adhesive gelatin matrix, wherein the matrix has opposing surfaces such that one surface of the matrix is affixed to one surface of the occlusive structure with the other surface of the matrix being adapted to cover and be in contact with tissue. In such aspects the occlusive device may be a plastic film for example.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from the detailed description.

DETAILED DESCRIPTION OF THE EMBODIMENTS

Figure 1:
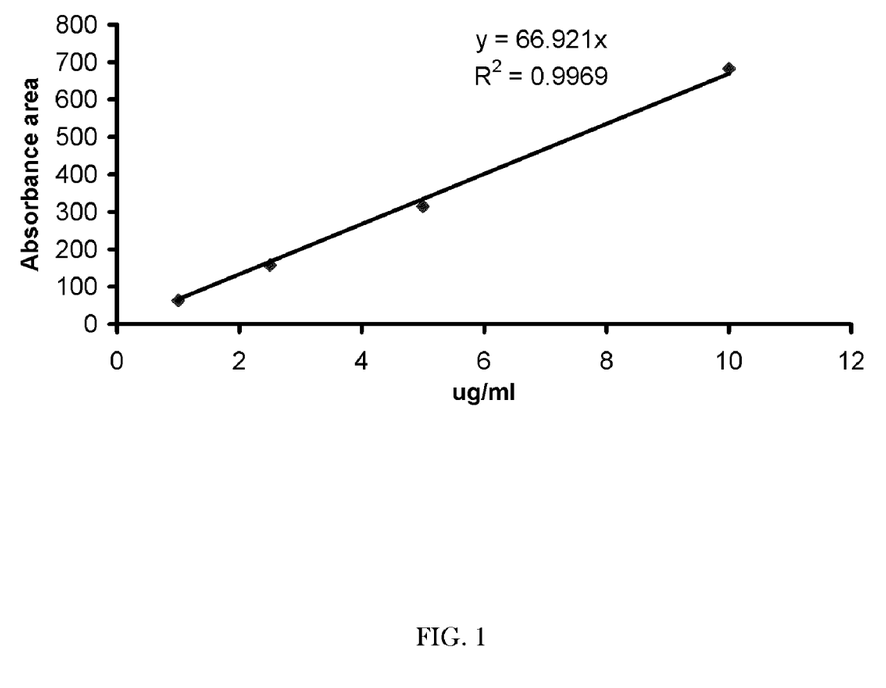
FIG. 1 is an HPLC/UV standard curve of sirolimus.
Figure 2:
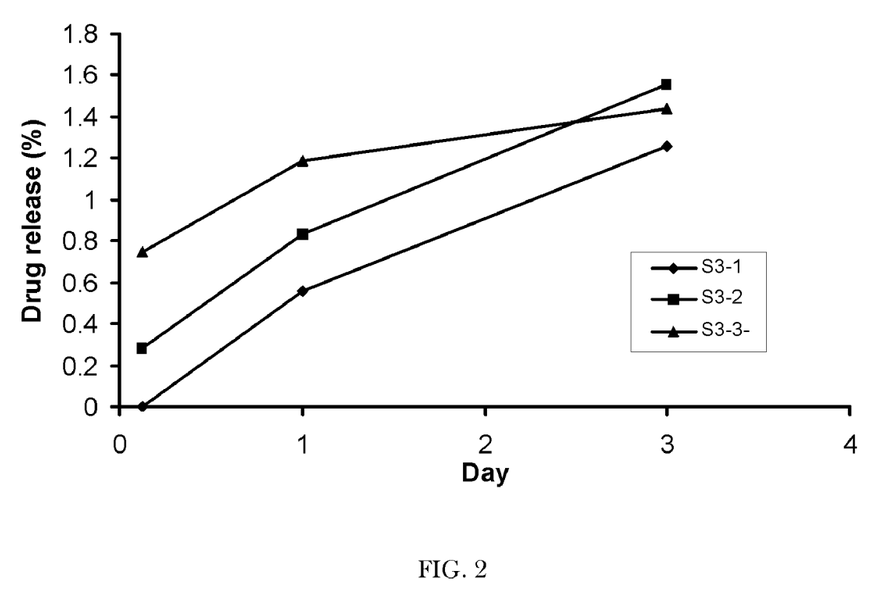
FIG. 2 shows sirolimus release from a gelatin wrap. S3-1, S3-2 and S3-3 were triplicate experiments of samples and every point was the average of duplicate HPLC analysis.
Figure 3:
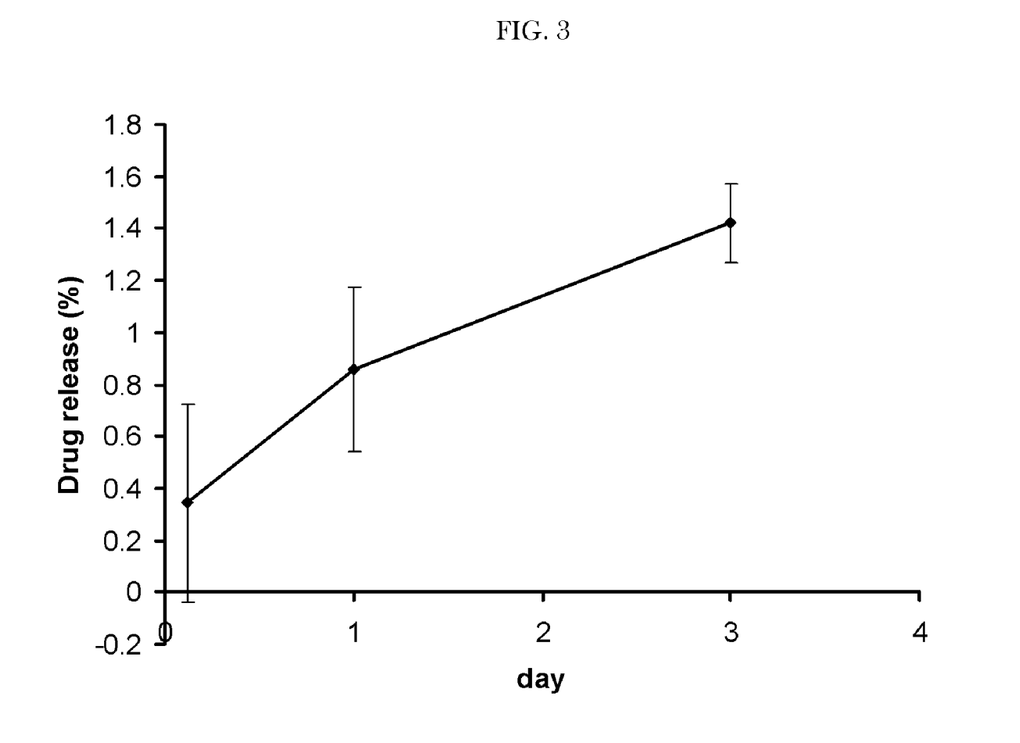
FIG. 3 shows average drug release from a gelatin wrap.

The present invention is a novel substantially non-adhesive elastic protein containing matrix that is biocompatible. In embodiments of the invention, the matrix is an elastic gelatin matrix that retains its elasticity such that it can be configured in a variety of manners as is required in various clinical conditions. As such the elastic gelatin matrix of the invention is flexible and has a variety of clinical uses for the treatment of a variety of conditions. Furthermore, the matrix of the invention can be configured into a variety of formats and used in conjunction with other devices or structures. The matrix of the invention may also have a variety of pharmaceuticals, chemicals and/or other agents incorporated into the matrix as desired for a variety of clinical applications. The gelatin matrix of the invention is also substantially non-adhesive meaning that the matrix does not substantially adhere to wounds, tissues (such as but not limited to skin, blood vessels and bone) and organs. Lastly, the matrix of the invention is absorbent, stable in vivo and in vitro and can be fabricated with a tensile strength and elasticity as required for a desired clinical application.

The elastic matrix of the invention is made from a solution comprising protein or a mixture of proteins, biocompatible polymer(s), cross-linking agent(s), solvent(s) and optionally plasticizer(s). The protein for use in the invention is selected from collagen, denatured collagen (i.e. gelatin) and mixtures thereof that are further admixed together with one or more biocompatible polymers. Plasticizers may be optionally added. The solution is lyophilized to essentially remove any solvent and provide the non-adhesive elastic gelatin matrix of the invention.

In aspects of the invention the biocompatible polymers for use in the invention are selected from the group consisting of polyethylene glycol (PEG), poly-L-lysine, poly-D-lysine, alginate, chitosan, hyaluronic acid, chondroitin sulfate and mixtures thereof.

In aspects of the invention the cross-linking agents for use in the invention are selected from the group consisting of 1-[3-(dimethylamino)propyl]-3-ethyl carbodiimide (EDC), N-hydroxysuccinimide (NHS), formaldehyde, glutaraldehyde, polyaziridines, diglycidyl ethers and mixtures thereof. In embodiments, EDC and NHS are used in combination as the cross-linking agent.

In aspects of the invention the optional plasticizer for use in the present invention is selected from the group consisting of glycerol, propylene glycol, sorbitol and mixtures thereof.

In aspects of the invention the solvent for use in the present invention is selected from the group consisting of water, methanol, ethanol, isopropanol, dimethylsulfide (DMS), and mixtures thereof. In aspects of the invention the solvent is water or if used in addition with a polar organic solvent, the solvent ratio is typically about 9:1, water to polar organic solvent, in the final mixture.

The solution of collagen and/or gelatin together with the biocompatible polymer(s), cross-linking agent(s), optional plasticizer(s) and solvent(s) are mixed and frozen, and then freeze-dried (i.e. lyophilized). The matrices so produced are substantially non-adhesive and elastic.

The ranges for the amounts of protein (collagen or gelatin), the amount of biocompatible polymer, the amount of solvent and the amount of optional plasticizer in the composition solution and in the lyophilized final composition may be as follows:

|  | % by weight in initial composition | % by weight in lyophilized non-adhesive elastic gelatin matrix, lyophilized |
| --- | --- | --- |
| Protein -collagen or denatured collagen (i.e. gelatin) | 0.5-30% | 50-90% |
| Biocompatible polymer | up to about 10% | up to about 40% (in aspects about 10-40%) |
| Cross-linking agent | 0.1-2% | 0.5-5% |
| Solvent | 50-99% | up to about 10% |
| Plasticizer (optional) | 0-5% | 0-10% |

*Note that the ranges provided in the table above for each of the protein, biocompatible polymer, cross-linking agent, solvent and plasticizer includes any sub ranges of the ranges listed.

The non-adhesive elastic gelatin matrix of the invention is made by combining solutions of protein, biocompatible polymers and cross-linking agents in a suitable solvent. The solutions of the various constituents of the matrix as described in the examples are aqueous, however, in aspects of the invention the biocompatible polymer(s) and cross-linking agent(s) may be first dissolved in a polar organic solvent such as but not limited to methanol, ethanol, isopropanol and dimethyl sulfoxide (DMSO), and in such a case, the solvent ratio of the final mixture is typically 9:1 in favor of water.

In aspects of the invention, solutions of the protein and biocompatible polymer are mixed and incubated for a time period at a temperature such that the protein does not set, i.e. form a gel. Temperatures of about 55° C. are suitable for such incubation. Should polyethylene glycol (PEG) be used as a biocompatible polymer, the PEG is typically added to the mixing and incubating protein solutions. A solution of cross-linking agent is then added and the resultant mixture is mixed for a period of time until a consistent gel is formed. The gel is then poured into a suitable mold and kept at room temperature for about 10 minutes and subsequently cooled at about 4° C. for a time period ranging from about 30 minutes up to about 12 hours. The mixture is washed to remove soluble components such as residual PEG and cross-linking agent and lyophilized for a period of about 24 hours or more until the final moisture content of the non-adhesive elastic gelatin matrix is less than about 10%. It is understood by one of skill in the art that the final moisture content of the resultant matrix (lyophilized matrix) can be adjusted to any value up to about 10% by weight of the matrix.

The non-adhesive elastic gelatin matrix of the invention can be developed to be drug-eluting on tissues and organs, including but not limited to, skin, tissue lacerations, surgical wounds of skin, tissue and organs, blood vessels and bone. In this embodiment, the matrix can be fabricated to have pharmaceutical, chemical and/or other agent incorporated therein. In one aspect, the pharmaceutical, chemical and/or other agent can be incorporated in an amount of about 0.1% to about 10% into the initial formulation step or about 1.0% to about 25% after drying. In another aspect the lyophilized matrix can be soaked in a solution of the desired pharmaceutical, chemical and/or other agent and then the matrix may be re-lyophilized. Desirable agents for use in conjunction with the present invention include but are not limited to silver ions, metallic silver or a silver salt, chlorohexidine, triclosan, povidone-iodine, other antimicrobial metals such as copper, platinum, gold, bismuth-based compounds, anesthetics such as lidocaine, antibiotics, immunosuppressants, antiproliferative agents, anti-inflammatory agents, antivirals and combinations thereof. The selection of the agent for use with the matrix of the invention will depend on its end use. For example, if used for the treatment of age-related conditions, an anti-ageing agent may be provided to the matrix before and/or after lyophilization. Such an anti-aging agent may be selected to treat for example fine lines, wrinkles and skin discolorations. In this aspect a suitable anti-aging agent may be selected from exfoliants, Vitamin A, Vitamin C, etc. If used to treat brown spots or discoloration an agent such as hydroquinone may be suitable for incorporation into the matrix.

The non-adhesive elastic gelatin matrix of the invention can be fabricated in a variety of forms such as a film, sheet, tube or sponge. The matrix of the invention may be used for example but not limited to a wound barrier, wound dressing, vascular wrap and combinations thereof. The matrix of the invention may also be used to reduce chronic inflammation, absorb exudates and/or promote a moist wound environment. The matrix of the invention can also be fabricated as a device in conjunction with other materials such as but not limited to polymer sheets, films, threads, membranes or meshes of silicone, polyurethane, polyethylene, Dacron™, nylon, silk, cellulose and combinations thereof. This may be carried out by chemically modifying the surface of the other material by methods of gamma irradiation, plasma or corona discharge and/or by UV light so that reactive groups are introduced onto the surface of the material. The reactive groups can then be covalently linked to complementary reactive groups present on the non-adhesive elastic matrix of the present invention by methods as described in the Applicant's International Application No. PCT CA02/00246 (the disclosure of which is incorporated herein by reference in its entirety).

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Without intending to be limiting in scope, the following examples serve to illustrate various embodiments of the invention.

Materials

Gelatin was purchased from Vyse Gelatin Company (5010 North Rose St., Schiller Park, Ill. 60176). Gelatin (300 Bloom) was obtained by the partial hydrolysis of a collagen derived from porcine sources: skin, white connective tissues and bones of animals and processed to yield a pharmaceutical grade gelatin. Sodium alginate (sodium salt) from *Macrocystis pyrifera* (high viscosity, 2% solution at 25° C. approx 14,000 cps) was purchased from Sigma Co. (St. Louis, Mo.). Polyethyleneglycol (Average Mn=3,400), 1-[3-(dimethylamino)propyl]-3-ethylcarbodiimide hydrochloride (EDC) and N-hydroxysuccinimide (NHS) and silver lactate were purchased from Aldrich Co. (Milwaukee, Wis. 53201).

Example 1

(Gelatin+Alginate+PEG 3400) Dressing

Stock Solutions:
Gelatin: 20% (w/v)

Alginate: 3.12% (w/v)
PEG 3400: 63% (w/v)
EDC/NHS: 40% (w/v) and 6% (w/v), respectively, (molar ratio: 4/1)
Composition of Water-Saturated Matrix:
Gelatin: 10% (w/w)
Alginate: 1.1% (w/w)
PEG: 7.2% (w/w)
Matrix Synthesis (e.g. To Form About 200 ml of Gel):

Gelatin (100 mL) and alginate (71.2 mL) solutions were mixed and incubated at 55° C. for 30 min. Then 30 mL of PEG 3400 solution was added and mixed. Afterward, 5 mL of fresh EDC/NHS solution was added to the mixture during mixing for 30 seconds. The about 200 ml of gel was poured into a mold and kept at room temperature for 10 min and subsequently cooled at 4° C. for 30 min. The matrix was washed in water overnight to remove soluble components such as PEG and cross-linking agent. Finally, the matrix was lyophilized. Typically, 0.32 ml of gel mixture yields 1 cm² of matrix surface area.

Example 2

(Gelatin+Alginate+PEG 3400+Glycerol) Dressing

Stock Solution:
Gelatin: 20% (w/v)
Alginate: 3.12% (w/v)
PEG 3400: 63% (w/v)
EDC/NHS: 40% (w/v) and 6% (w/v), respectively, (molar ratio: 4/1)
Glycerol: 10% (w/v)
Composition of Water-Saturated Matrix:
Gelatin: 10% (w/w)
Alginate: 1.1% (w/w)
PEG: 7.2% (w/w)
Poly-Lysine: 0.1% (w/w)
Matrix Synthesis (e.g. 200 ml of Gel)

Gelatin (100 mL) and alginate (71.2 mL) solutions were mixed and incubated at 55° C. for 30 min. Then 30 mL of PEG 3400 solution was added and mixed. Afterward, 5 mL of fresh EDC/NHS solution was added to the mixture during mixing for 30 seconds. The about 200 ml of gel was poured into a mold and kept at room temperature for 10 min and subsequently cooled at 4° C. for 30 min. The matrix was washed in water overnight to remove soluble components such as PEG and cross-linking agent. Usually, 0.32 ml of gel mixture yields 1 cm² of matrix surface area. The matrix was soaked in 2.85 L of 10% glycerol (4.4 ml of glycerol per 1 cm² of gel). Finally the matrix was lyophilized.

Example 3

(Gelatin+Alginate+PEG 3400+Poly-L-lysine) Dressing

Stock Solution:
Gelatin: 20% (w/v)
Alginate: 3.12% (w/v)
PEG 3400: 63% (w/v)
Poly-L-Lysine: 2% (w/v)
EDC/NHS: 40% (w/v) and 6% (w/v), respectively, (molar ratio: 4/1)
Composition of Water-Saturated Matrix:
Gelatin: 10% (w/w)
Alginate: 1.1% (w/w)
PEG: 7.2% (w/w)
Poly-lysine: 0.1% (w/w)
Matrix Synthesis Gelatin and alginate solutions were mixed as in previous examples. Then 10 ml of 2% poly-L-lysine was added with mixing. 30 ml of PEG 3400 was added to the mixture and mixed. The remaining procedures to yield the final matrix were identical to previous examples.

Example 4

(Gelatin+Alginate+PEG3400+Poly-L-lysine+Glycerol) Dressing

Stock Solution:
Gelatin: 20% (w/v)
Alginate: 3.12% (w/v)
PEG 3400: 63% (w/v)
Poly-L-Lysine: 2% (w/v)
EDC/NHS: 40% (w/v) and 6% (w/v), respectively, (molar ratio: 4/1)
Glycerol: 10% (w/v)
Composition of Water-Saturated Matrix:
Gelatin: 10% (w/w)
Alginate: 1.1% (w/w)
PEG: 7.2% (w/w)
Poly-L-lysine: 0.1% (w/w)
Matrix Synthesis Gelatin and alginate solutions were mixed as in previous examples. Then 10 ml of 2% poly-L-lysine was added with mixing. 30 ml of PEG 3400 was added to the mixture and mixed. The remaining procedures to yield the hydrated and washed matrix were identical to previous examples. Finally, the matrix was soaked in 2.85 L of 10% glycerol (4.4 ml of glycerol per 1 cm² of gel) and then lyophilized.

Example 5

(Gelatin+Alginate) Dressing

Stock Solution:
Gelatin: 1% (w/v)
Alginate: 10% (w/v)
EDC/NHS: 40% (w/v) and 6% (w/v), respectively, (molar ratio: 4/1)
Composition of Water-Saturated Matrix:
Gelatin: 0.9% (w/w)
Alginate: 0.1% (w/w)
Matrix Synthesis (e.g. 200 ml of Gel)

Gelatin (180 mL) and alginate (20 mL) solutions were mixed and incubated at 55° C. for 30 min. Afterward 1.4 ml of fresh EDC/NHS solution was added to the mixture with mixing for 1 minute. The mixture was poured into a mold (10 ml per 20 cm² area), and then frozen at −20° C. overnight. Finally, the matrix was lyophilized.

The various matrices as in Examples 1-5 can be poured (prior to the initial cooling/freezing step) directly over other materials (without modification as outlined above), such as but not limited to polymer sheets, films, threads, membranes or meshes of silicone, polyurethane, polyethylene, Dacron™, nylon, silk, cellulose and combinations thereof, that may or may not contain added agents, such as therapeutics, silver-containing materials or other medicaments so as to embed the mesh, net or fibers within the matrices of examples 1-5.

Example 6

In Vitro Degradation of Gelatin Sponge by Collagenase

The degradation of cross-linked gelatin-based materials was studied using bacterial collagenase. The collagenase used in this study was from *Clostridium* (EC 3.4.24.3) and had an activity of 362 U/mg solid. Samples (50 mg) were incubated at 37° C. in 10 mL of collagenase solution with concentration of 15.35 U/mg in 0.1 M Tris-HCl buffer (pH=7.4) containing 0.005 M $CaCl_2$ and 0.05 mg/mL sodium azide. After each incubation interval, the sample was carefully washed three times with de-ionized water and lyophilized overnight. The extent of degradation was expressed as the percentage of weight remaining after degradation.

The biodegradation of gelatin-based dressings in accordance with the present invention was rapid in the presence of collagenase, as would be expected. For nearly all of the matrices, approximately 80% of the gelatin sponge was degraded in the first 24 hours. The gelatin matrix containing gelatin and aliginate appeared less affected by the action of collagenase (Table 1).

TABLE 1

Biodegradation of gelatin dressings at specified times (expressed as % of weight remaining) in the presence of collagenase.

| Sample Matrix | 0 hr | 24 hr | 48 hr | 72 hr |
| --- | --- | --- | --- | --- |
| 1% Gelatin + Alginate | 100 | 96.1 | 75.9 | 65.4 |
| 10% Gelatin + PEG + Alginate | 100 | 21.0 | 22.2 | 17.4 |
| 10% Gelatin + PEG + Alginate + Glycerol | 100 | 23.3 | 12.8 | 21.8 |
| 10% Gelatin + PEG + Alginate + Glycerol + Poly-L-Lysine | 100 | 18.4 | 14.3 | 14.4 |
| 10% Gelatin + PEG + Alginate + Poly-L-Lysine | 100 | 16.5 | 14.8 | 12.6 |

Example 7

Determination of Water Uptake Ability

To determine the water uptake ability of the dressing, about 40 mg of dressing was placed in a 20 ml glass vial to which was added 15 ml of water or PBS (0.01M, pH=7.4). The sample was weighed after hydration for 5 min at room temperature and then incubated at 37° C. for 4 hr and 24 hr. The sample was weighed at both incubation intervals. The water uptake ability is expressed as the weight ratio of absorbed water to dry dressing (Table 2). Matrices particularly without platiciser are all very absorbent and can soak up to approximately 30-35 times their weight in water in about 24 hours.

TABLE 2

Water uptake at specified times, grams of water/grams of matrix (g/g)

| Sample Matrix | 5 min (g/g) | 4 hr (g/g) | 24 hr (g/g) |
| --- | --- | --- | --- |
| 1% Gelatin + Alginate | 31.6 | — | 28.7 |
| 10% Gelatin + PEG + Alginate | 16.2 | 27.3 | 32.1 |

TABLE 2-continued

Water uptake at specified times, grams of water/grams of matrix (g/g)

| Sample Matrix | 5 min (g/g) | 4 hr (g/g) | 24 hr (g/g) |
| --- | --- | --- | --- |
| 10% Gelatin + PEG + Alginate + Glycerol | 2.5 | 10.8 | 11.7 |
| 10% Gelatin + PEG + Alginate + Poly-L-Lysine | 9.0 | 29.9 | 34.6 |
| 10% Gelatin + PEG + Alginate + Poly-L-Lysine + Glycerol | 1.8 | 9.6 | 10.5 |

*values are a ratio, value:1.

Example 8

Determination of Water Solubility

To determine the water solubility of the dressing, place a sample with a known weight was placed into a glass vial to which 15 mls of water was added. This was incubated at 40° C. for 24 hr and then the water removed and the sample washed twice with water. The sample was then dried in a 100° C. oven to a constant weight and then re-weighed. The water solubility is typically expressed as percentage of weight lost after water treatment (Table 3). The matrices exhibited a good water solubility providing an indication of its clinical longevity. Lower solubility resulted in a more stable matrix at body temperature. Thus such matrices can be removed from a wound for example as a single sheet after 24 hours or more with minimum patient discomfort. While all matrices demonstrated good stability, those without plasticizer were even more stable.

TABLE 3

Stability of 10% gelatin-based materials after incubation in 40° C. water for 24 hr.

| Sample Matrix | W1 (g) | W2 (g) | Weight Remaining (%) | Water Solubility (%) |
| --- | --- | --- | --- | --- |
| 1% Gelatin + Alginate | 0.0315 | 0.0260 | 83.4 | 16.6 |
| 10% Gelatin + PEG + Alginate | 0.0335 | 0.0261 | 77.9 | 22.1 |
| 10% Gelatin + PEG + Alginate | 0.0308 | 0.0235 | 76.3 | 23.7 |
| 10% Gelatin + PEG + Alginate + Glycerol | 0.0448 | 0.0107 | 23.9 | 76.1 |
| 10% Gelatin + PEG + Alginate + Glycerol | 0.0443 | 0.0108 | 24.4 | 75.6 |
| 10% Gelatin + PEG + Alginate + Poly-L-Lysine | 0.0364 | 0.0305 | 83.8 | 16.2 |
| 10% Gelatin + PEG + Alginate + Poly-L-Lysine | 0.0361 | 0.0294 | 81.4 | 18.6 |
| 10% Gelatin + PEG + Alginate + Poly-L-Lysine + Glycerol | 0.0504 | 0.0115 | 22.82 | 77.2 |
| 10% gelatin + PEG + Alginate + Poly-L-Lysine + Glycerol | 0.0507 | 0.0124 | 24.5 | 75.5 |

Note:
W1: weight of original sample
W2: weight of dried sample after treatment
Weight Remaining = (W2/W1) × 100%
Water solubility = (1 − W2/W1) × 100%

Example 9

Determination of Mechanical Properties

The mechanical properties were determined for the tensile strength and elongation at break of hydrated gelatin matrices (4.5 cm×1 cm), which had been soaked in 0.01M, pH=7.4 PBS buffer solution for 1 hour at room temperature. A 0.5 kg load cell was used with an extension rate of 5 mm/min (Table 4). This example demonstrates that tensile strength and elasticity of the matrices can be adjusted through the variation of the amount and combination of components of the matrix. This is valuable for providing matrices for a variety of clinical applications such as an artificial skin or wound dressing.

TABLE 4

Mechanical properties of gelatin-based dressings.

| Sample No. | Tensile Strength (g/cm$^2$) | Elongation at Break (%) |
| --- | --- | --- |
| 1% Gelatin + Alginate | 25.5 | 53.0 |
| 10% gelatin + PEG | 30.5 | 126.8 |
| 10% Gelatin + PEG + Alginate | 73.8 | 174.9 |
| 10% Gelatin + PEG + Alginate + glycerol | 83.8 | 155.4 |
| 10% Gelatin + PEG + Alginate + Poly-L-Lysine | 111.4 | 176.3 |
| 10% Gelatin + PEG + Alginate + Poly-L-Lysine + glycerol | 148.8 | 193.3 |

Example 10

Addition of Sirolimus to Gelatin-Based Dressings

Examples 1-5 are directed to the manufacture of a range materials that may be used as carriers for various medicaments such as the antiproliferative and anti-inflammatory drug Sirolimus (Rapamycin) for delivery to the surface of tissues and organs. While the drug Sirolimus is used in this example, it is noted that other drugs may be used either alone or in combination to be delivered to the surface of tissues and organs.

Stock Solution:
Gelatin: 1% to water
Alginate: 1% to 0.05N NaOH
EDC/NHS: 400 mg/60 mg per 1 ml of 10 mM of Mes saline solution (pH=4.5)
Glycerol: 1% (in water).
The Formulation in the Matrix:
Gelatin: 0.9% (w/v)
Alginate: 0.1% (w/v)
Water
Procedure
Preparation of Stock Solutions
Solution 1: 2 g of gelatin was added to 180 ml of water; after gelatin was completely hydrated in water, the mixture was incubated at 50° C. to dissolve the gelatin.
Solution 2: 0.2 g of alginate was added into 20 ml of 0.05 N NaOH, and incubated at 50° C. to dissolve the alginate.
Solution 3: 400 mg of EDC+60 mg of NHS was added into 1 ml of 10 mM Mes saline solution (pH=4.5).
Solution 4: 2 g of glycerol was added into 200 ml of water
Matrix Synthesis (e.g. 200 ml of Gel)
1. Solution 1 and Solution 2 were mixed and incubated at 55° C. for 30 min. Afterward, 1.379 ml of fresh EDC/NHS solution was added to mixture with mixing for 1 minute. The mixture was poured into a mold (9 ml per 20 cm$^2$ a, then froze at −20 degrees ° C. for overnight.
2. Cross-linked gel was washed by Milli-Q water 4 times with 500 ml per matrix (Refresh water every 1 hr); the matrix was refrozen at room temperature, soaked in 9 ml of 1% glycerol per 20 cm$^2$ gel. Then gel was frozen again at −20° C. and lyophilized. The matrix may be prepared as a thin film.

Sirolimus Loading of Matrices:
The above matrix, (or any of the matrices of examples 1-5) was cut into 1×4 cm square. Afterwards, 80 ul of drug solution (1 mg/80 ul ethanol) was added on the surface of the material, or the material was immersed in a solution of drug. After drug loading into the film, the film was allowed to dry and the drug-loaded film was exposed to gamma-irradiation for 8 hr (25 KGy).

In-Vitro Drug Release Study
Procedure:
1. Preparation of Samples
1) One matrix (1×4 cm) was cut into equal 3 pieces.
2) Dissolve 1 mg of drug in 90 ul of ethanol.
3) Adding 30 ul of drug solution into each matrix piece of step 1.
4) Evaporate Ethanol.
2. Drug Release Study
1) Place samples in 15 ml of Falcon tubes.
2) Add 5 ml of PBS (10 mM, pH=7) to each tube.
3) Incubate tubes at 37° C. for 10 days.
4) Withdraw samples of 2.5 ml at intervals of 3 hr, 1 day, 3 days, 5 days, 7 day, 9 days, and 2.5 ml fresh PBS was replaced for samples taken.
5) HPLC analysis of samples.
Column: Hypersil ODS, 100×2.1 mm
Flow rate: 0.2 ml/min
Detection: UV, 278 nm
Mobile phase: 600 ml acetonitrile and 400 ml of water
Temperature: 50° C.
Injection volume: 10 μl
Sirolimus Standards: 0 ug/ml, 1 ug/ml, 2.5 ug/ml, 5 ug/ml 10 ug/ml
Analysis: Each sample was injected two times for analysis. Each data point is the average of 6 replicate tests.

Although preferred embodiments of the invention have been described herein in detail, it will be understood by those skilled in the art that variations may be made thereto without departing from the spirit of the invention or the scope of the appended claims.

The inention claimed is:
1. An elastic non-adhesive protein matrix comprising:
(a) about 50-90% by wgt of one or more proteins selected from the group consisting of collagen, and denatured collagen and mixtures thereof;
(b) about 10-40% by wgt of one or more biocompatible polymers selected from the group consisting of polyetheylene glycol, poly-L-lysine, alginate, chitosan, hyaluronic acid, and chondroitin sulfate and mixtures thereof; and
(c) about 0.5-5% by wgt of diglycidyl ether;
wherein the matrix is lyophilized after addition of (c) to result in a matrix that is non-adherent to wounds tissues, and organs and can be removed after 24 hours.
2. The matrix of claim 1, wherein the matrix additionally comprises one or more plasticizers.
3. The matrix of claim 1, wherein said matrix contains less than 10% moisture content.
4. The matrix of claim 2, wherein said plasticizer is provided in an amount of up to 10% by weight of said matrix.

5. The matrix of claim 1, wherein said matrix is provided as a film, sheet, tube or sponge.

6. The matrix of claim 1, wherein said matrix is provided together with a material selected from the group consisting of polymer sheets, polymer films, threads, silicone membranes, silicone meshes, polyurethane, polyethylene, polyethylene terephthalate, nylon, silk, and cellulose and combinations thereof.

7. The matrix of claim 1, wherein said matrix is provided as a wound dressing, wound barrier, tissue cover or vascular cover.

8. The matrix of claim 1, wherein said matrix absorbs exudates.

9. The matrix of claim 1, wherein said matrix promotes a moist environment.

10. A method for making a non-adhesive elastic protein matrix, the method comprising, in order, the steps of:
   (a) mixing collagen, denatured collagen, or a combination thereof in a solution and heating said solution;
   (b) adding polyethylene glycol, poly-L-lysine, alginate, chitosan, hyaluronic acid, or chondroitin sulfate or any combination thereof to the solution of (a);
   (c) adding 1-[3-(dimethylamino)propyl]-3-ethyl carbodiimide (EDC), N-hydroxysuccinimide (NHS), formaldehyde, glutaraldehyde, a polyaziridine, or a diglycidyl ether or any combination thereof to the solution of (b) under conditions that induce protein cross-linking while maintaining a solution;
   (d) mixing (c) until a pourable gel is formed;
   (e) cooling the gel of (d); and
   (f) lyophilizing the cooled gel of (e) to form the non-adhesive elastic protein matrix;
   wherein the non-adhesive elastic protein matrix comprises:
      about 50-90% by wgt collagen or denatured collagen or a combination thereof;
      about 10-40% by wgt polyetheylene glycol, poly-L-lysine, alginate, chitosan, hyaluronic acid, or chondroitin sulfate or any combination thereof;
      about 0.5-5% by wgt of 1-[3-(dimethylamino)propyl]-3-ethyl carbodiimide (EDC), N-hydroxysuccinimide (NHS), formaldehyde, glutaraldehyde, a polyaziridine, or a diglycidyl ether or any combination thereof; and
   wherein the matrix is non-adherent to wounds, tissues and organs and can be removed after 24 hours.

11. The method of claim 10, wherein one or more plasticizers is added to the solution of (b), and/or the solution of (c), or both.

12. The method of claim 10, wherein the one or more cross-linking agents comprise diglycidyl ether.

13. A method for making a non-adhesive elastic protein matrix, the method comprising, in order, the steps of:
   (a) mixing 0.5-30% by wgt collagen or denatured collagen; up to 10% by wgt of one or more biocompatible polymers; 0.1-2% by wgt of one or more cross-linking agents; about 50% to about 99% by weight solvent; and optionally up to 5% by weight plasticizer in a solution until a pourable gel is formed;
   (b) cooling the gel of (a); and
   (c) lyophilizing the cooled gel of (b) to form the non-adhesive elastic protein matrix that is removable after 24 hours.

14. The method of claim 13, wherein the one or more cross-linking agents comprise diglycidyl ether.

15. A method for making a non-adhesive elastic protein matrix, the method comprising, in order, the steps of:
   (a) mixing collagen or denatured collagen or a combination thereof in a solution and heating said solution;
   (b) adding polyethylene glycol, poly-L-lysine, alginate, chitosan, hyaluronic acid, or chondroitin sulfate or any combination thereof to the solution of (a);
   (c) adding one or more cross-linking agents selected from the group consisting of 1-[3-(dimethylamino)propyl]-3-ethyl carbodiimide (EDC), N-hydroxysuccinimide (NHS), formaldehyde, glutaraldehyde, a polyaziridine, and a diglycidyl ether or any combination thereof to the solution of (b);
   (d) cooling the solution of (c); and
   (e) lyophilizing the cooled solution of (d) to form the non-adhesive elastic protein matrix that can be removed after 24 hours.

16. The method of claim 15, wherein the one or more cross-linking agents comprise diglycidyl ether.

* * * * *